(12) United States Patent
Lee et al.

(10) Patent No.: US 7,968,081 B2
(45) Date of Patent: Jun. 28, 2011

(54) PEPTIDE FOR DIAGNOSING, PREVENTING AND TREATING ATHEROSCLEROSIS AND USES THEREOF

(75) Inventors: Byung Heon Lee, Daegu (KR); In San Kim, Daegu (KR); Hai Yan Hong, Daegu (KR); In Seop So, Daegu (KR)

(73) Assignee: Kyungpook National University Industry—Academic Cooperation Foundation, Daegu (KR)

( * ) Notice: Subject to any disclaimer, the term of this patent is extended or adjusted under 35 U.S.C. 154(b) by 382 days.

(21) Appl. No.: 12/009,359

(22) Filed: Jan. 18, 2008

(65) Prior Publication Data

US 2009/0074663 A1    Mar. 19, 2009

(30) Foreign Application Priority Data

Apr. 5, 2007    (KR) .................. 10-2007-0033592

(51) Int. Cl.
*A61K 51/00* (2006.01)
*A61M 36/14* (2006.01)

(52) U.S. Cl. ............... 424/1.69; 424/1.11; 424/1.65; 424/1.81; 424/1.85; 424/1.89; 424/9.1; 530/300; 530/328

(58) Field of Classification Search ........... 424/1.11, 424/1.65, 1.69, 1.73, 1.81, 1.85, 1.89, 9.1, 424/9.2, 9.3, 9.4, 9.5, 9.6, 9.7, 9.8; 530/300, 530/328; 514/1, 2, 5, 7, 9, 15; 206/223, 206/569, 570

See application file for complete search history.

(56) References Cited

U.S. PATENT DOCUMENTS

2009/0074663 A1 * 3/2009 Lee et al. .................. 424/1.69

OTHER PUBLICATIONS

Chamberlain et al, Am. Heart J, 2010, vol. 159, pp. 850-856.*
Schaefer et al, Herz, 2010, vol. 35, pp. 192-197.*
Hitzeman, R., et al., "Isolation and Characterization of the Yeast . . . ", J. Biol. Chem., 1980, pp. 12073-12080, vol. 255, Am Society for Biochemistry and Molecular Biology, USA.
Wilson, J., et al., "Hepatocyte-directed Gene Transfer in Vivo Leads . . . ", J. Bio. Chem., 1992, pp. 963-967, vol. 267, Am. Society for Biochemistry and Molecular Biology, USA.
Wu and Wu, "Receptor-mediated Gene Delivery and Expression in Vivo", J. Bio. Chem., 1988, pp. 14621-14624, vol. 263, Am. Society for Biochemistry and Molecular Biology, USA.
Paul, W.E., "Interleukin-4: a Prototypic Immunoregulatory Lumphokine", Blood, 1991, pp. 1859-1870, vol. 77, Am. Society of Hematology, USA.
Sasaguri, T., et al., "A Role for Interleukin 4 in Production . . . ", Atherosclerosis, 1998, pp. 247-253, vol. 138, Elsevier Science Ireland Ltd.
Lee, Y., et al., "IL-4-induced Oxidative Stress Upregulates . . . ", J. Mol. Cell Cardiol., 2001, pp. 83-94, vol. 33, Academic Press, USA.
Davenport, P., et al., "The Role of Interleukin-4 and Interleukin-12 . . . ", Am. J. Pathol., 2003, pp. 1117-1125, vol. 163, Am. Society for Investigative Pathology, USA.
King, V., et al., "Interleukin-4 Deficiency Decreases . . . ", Arterioscler Thromb Vasc Biol, 2002, pp. 456-461, vol. 22, American Heart Association, USA.
Nelms, K., et al., "The IL-4 Receptor: Signaling Mechanisms . . . ", Annu Rev Immunol, 1999, pp. 701-738, vol. 17, Annual Reviews, USA.
Smith, G., Filamentous Fusion Phage: Novel Expression Vectors . . . , Science, 1985, pp. 1315-1317, vol. 228, USA.
Matter, C., et al., "Molecular Imaging of Atherosclerotic Plaques Using a Human . . . ", Circulation Research, 2004, pp. 1225-1233, vol. 95, American Heart Association, USA.
Joshi, B., et al., "In Situ Expression of Interleukin-4 (IL-4) Receptors . . . ", Cancer Research, 2001, pp. 8058-8061, 61, USA.

* cited by examiner

*Primary Examiner* — D L Jones
(74) *Attorney, Agent, or Firm* — IpHorgan Ltd.

(57)    ABSTRACT

A peptide for diagnosing, preventing and treating atherosclerosis, and a use thereof, comprising an amino acid sequence as set forth in SEQ ID NO: 1 or SEQ ID NO: 2, and a use thereof. The peptide effectively targets atherosclerotic plaques, and binds to IL-4R to thereby exhibit antagonistic effects on IL-4-mediated signaling of cellular inflammatory reaction and survival reaction. The peptide of the present invention can be used for diagnosis of atherosclerosis, prevention and treatment of IL-4-induced inflammatory reaction and prevention and treatment of atherosclerosis which is primarily caused by the inflammatory reaction, as well as for prevention or treatment of atherosclerosis via conjugation with an anti-atherosclerotic drug.

17 Claims, 9 Drawing Sheets
(7 of 9 Drawing Sheet(s) Filed in Color)

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: peptide 1, completely synthesized

<400> SEQUENCE: 1
```

```
Cys Arg Lys Arg Leu Asp Arg Asn Cys
  1               5

<210> SEQ ID NO 2
<211> LENGTH: 9
<212> TYPE: PRT
<213> ORGANISM: Artificial Sequence
<220> FEATURE:
<223> OTHER INFORMATION: peptide 2, completely synthesized

<400> SEQUENCE: 2

Cys Pro Ser Asn Gly Lys Arg Asp Cys
  1               5

<210> SEQ ID NO 3
<211> LENGTH: 27
<212> TYPE: DNA
<213> ORGANISM: Artificial Sequence
<220> FEATURE:
<223> OTHER INFORMATION: nucleotide for peptide 1, completely
      synthesized

<400> SEQUENCE: 3
tgccgtaagc gtcttgatcg gaattgc                                         27

<210> SEQ ID NO 4
<211> LENGTH: 27
<212> TYPE: DNA
<213> ORGANISM: Artificial Sequence
<220> FEATURE:
<223> OTHER INFORMATION: nucleotide for peptide 2, completely
      synthesized

<400> SEQUENCE: 4
tgccggacta ggagtaagtc gggttgc                                         27

<210> SEQ ID NO 5
<211> LENGTH: 20
<212> TYPE: DNA
<213> ORGANISM: Artificial Sequence
<220> FEATURE:
<223> OTHER INFORMATION: 5' primer for sequencing, completely
      synthesized

<400> SEQUENCE: 5
agcggaccag attatcgcta                                                 20

<210> SEQ ID NO 6
<211> LENGTH: 20
<212> TYPE: DNA
<213> ORGANISM: Artificial Sequence
<220> FEATURE:
<223> OTHER INFORMATION: 3' primer for sequencing, completely
      synthesized

<400> SEQUENCE: 6
aacccctcaa gacccgttta                                                 20
```

US 7,968,081 B2

PEPTIDE FOR DIAGNOSING, PREVENTING AND TREATING ATHEROSCLEROSIS AND USES THEREOF

CROSS-REFERENCE TO RELATED APPLICATIONS

This application claims priority to and the benefit of Korean Patent Application No. 10-2007-0033592, filed on Apr. 5, 2007, the entire contents of which is incorporated herein by reference.

BACKGROUND OF THE INVENTION

1. Field of the Invention

The present invention relates generally to a peptide for diagnosing, preventing and treating atherosclerosis, and a use thereof. More specifically, the present invention relates to a peptide for diagnosing, preventing and treating atherosclerosis, comprising an amino acid sequence as set forth in SEQ ID NO: 1 or SEQ ID NO: 2, and a use thereof.

2. Background Art

Atherosclerosis is a disease which involves a build-up of fat on the artery walls over time and thickening of the artery walls. There are known several risk factors that contribute to the development of atherosclerosis. Hyperlipidemia, particularly hypercholesterolemia, is primarily responsible for the pathogenesis of atherosclerosis. Further, the onset of atherosclerosis may be caused by other factors such as hypertension and diabetes. With recent changes of dietary habits into Western style involving consumption of large amounts of meat, and the gradual ageing of the population, there is now a significant increase in the incidence of atherosclerosis and atherosclerosis-related cerebro-cardiovascular diseases. Upon reviewing the development and progress of atherosclerosis, various pathogenic factors including oxidized lipids, high blood pressure and rapid blood flow result in damage of vascular endothelial cells constituting an arterial inner surface, then gradually increasing deposits of fat on vessel walls, and finally arterial thickening arising from infiltration of macrophages and T cells, progression of inflammatory reactions and proliferation of vascular smooth muscle cells. As a result, blood vessels become narrower to thereby result in poor flow of blood. When narrowing of the cardiac coronary arteries takes place, overdoing exercise may cause an insufficient supply of blood to the heart, which is then accompanied by symptomatic pain of angina pectoris. Meanwhile, where the activity of proteases, produced by macrophages within the thickened arterial walls (called atherosclerotic plaques), is high, a portion of the tissues covering plaques is partially ruptured. Here, fatty materials and peripheral proteins in plaques may flow out into the blood vessels to thereby form thrombi (blood platelets) which will lead to frequent occlusion of coronary arteries or cerebral vessels, thus causing myocardial infarction or cerebral apoplexy.

Conventional atherosclerosis diagnosis is usually made via examination of target lesions including vascular narrowing and calcification, using ultrasonography or angiography. However, the conventional diagnostic method is applicable only after substantial progress of atherosclerosis has already been made to an extent that arterial narrowing is visible by naked eyes. Further, only the medical finding of the arterial narrowing is not helpful to determine whether lesions are stable plaques or otherwise unstable plaques (vulnerable plaques or rupturable plaques) that are likely to readily disrupt. Therefore, there is a need for development of a novel diagnostic method and a diagnostic agent for the same, which are helpful and beneficial to early finding and diagnosis of atherosclerosis before appearance of conspicuous arterial narrowing, by alleviation or removal of disadvantages of these conventional atherosclerotic plaque diagnostic methods, or to determination of stability of plaques.

Meanwhile, a drug delivery system for selective delivery of a drug to affected tissues, or a targeted therapy is attracting a great deal of attention. This is because it is possible to enhance the drug efficacy while achieving a significant reduction of adverse side effects of the drug on normal tissues, even with administration of the drug at the same dose. For instance, when a certain substance (such as peptide) which is targeted to atherosclerotic plaques is conjugated to an anti-atherosclerotic drug, the resulting complex will be able to be used as an intelligent drug delivery system. Examples of a conventional atherosclerosis therapy may include a method involving chronic administration of hyperlipidemia-lowering drugs, a method involving surgical removal of plaques in severe conditions and then insertion of a metal stent to prevent restenosis or re-narrowing of blood vessels, and the like. When a selective drug delivery system to plaques is conjugated with a drug capable of inhibiting proliferation of vascular smooth muscle cells (VSMCs), as an anti-atherosclerotic drug, and a drug capable of suppressing activity of macrophages or action of protease, the resulting conjugate will be useful to prevent excessive growth or rupture of plaques.

SUMMARY OF THE INVENTION

As a result of a variety of extensive and intensive studies and experiments to solve the problems as described above and develop an atherosclerotic plaque-targeting peptide that can be used for diagnosis of atherosclerotic plaques, the inventors of the present invention screened an atherosclerotic plaque tissue-specific peptide using a phage peptide display technique, and discovered that the resulting peptide not only can be usefully employed as an atherosclerotic plaque diagnostic means as well as an intelligent drug delivery system, but also can be usefully employed for diagnosis, prevention and treatment of atherosclerosis, due to having antagonistic effects on the interleukin-4 receptor (hereinafter, abbreviated as IL-4R). The present invention has been completed based on these findings.

Therefore, the present invention has been made in view of the above problems, and it is an object of the present invention to provide a peptide for diagnosis, prevention and treatment of atherosclerosis, and a use thereof.

In accordance with an aspect of the present invention, the above and other objects can be accomplished by the provision of a peptide for diagnosis, prevention and treatment of atherosclerosis.

In accordance with another aspect of the present invention, there is provided a composition for diagnosis of atherosclerosis, comprising the aforesaid peptide as an active ingredient.

In accordance with a further aspect of the present invention, there is provided a pharmaceutical composition for prevention and treatment of atherosclerosis, comprising the aforesaid peptide and an anti-atherosclerotic drug being conjugated to the peptide, as active ingredients.

In accordance with a still further aspect of the present invention, there is provided a kit for diagnosis of atherosclerosis, comprising the aforesaid peptide.

In accordance with a further aspect of the present invention, there is provided a method for detecting atherosclerotic plaques, comprising: injecting the aforesaid peptide into an individual subject; and detecting the location of the peptide in the subject.

In accordance with yet another aspect of the present invention, there is provided a composition for prevention and treatment of an IL-4-mediated inflammatory disease, comprising the aforesaid peptide as an active ingredient.

BRIEF DESCRIPTION OF THE DRAWING FIGURES

The patent or application file contains at least one drawing executed in color. Copies of this patent or patent application publication with color drawing(s) will be provided by the Office upon request and payment of the necessary fee.

FIG. 1 is a bar graph showing results of 3 and 4 consecutive runs for screening of phages exhibiting specific binding to atherosclerotic plaques, using a phage peptide display technique (an increase (-fold) is relative to a value of 1R).

A: Coronary artery-derived atherosclerotic plaques

B: Femoral artery-derived atherosclerotic plaques;

A: Fluorescence micrograph for murine aortic atherosclerotic plaque tissues with injection of a control peptide. Blue fluorescence represents nuclear DAPI staining, and an inserted small figure represents the results of Oil Red O staining of the same tissues.

B: Fluorescence micrograph for murine aortic atherosclerotic plaque tissues with injection of the peptide of the present invention. Green fluorescence (arrow) represents the peptide, blue fluorescence represents nuclear DAPI staining, and an inserted small figure represents the results of Oil Red O staining of the same tissues.

C: Differential interference contrast (DIC) fluorescence micrograph for murine aortic atherosclerotic plaque tissues with injection of a control peptide.

D: DIC fluorescence micrograph for murine aortic atherosclerotic plaque tissues with injection of the peptide of the present invention. Green fluorescence (arrow) represents the peptide.

E: Fluorescence micrograph for murine aortic atherosclerotic plaque tissues with injection of the peptide of the present invention, after double staining of the tissues with antibodies against vascular endothelial cells. Green fluorescence represents the peptide, red fluorescence represents staining of vWF (von Willebrand Factor) for vascular endothelial cells, and blue fluorescence represents nuclear DAPI staining. Inserted small figures represent enlarged micrographs.

F: Fluorescence micrograph for murine aortic atherosclerotic plaque tissues with injection of the peptide of the present invention, after double staining of the tissues with antibodies against macrophages. Green fluorescence represents the peptide, red fluorescence represents staining of Mac-3 for macrophages, and blue fluorescence represents nuclear DAPI staining.

G: Fluorescence micrograph for murine cerebral tissues with injection of the peptide of the present invention. Blue fluorescence represents nuclear DAPI staining.

Figure 4:
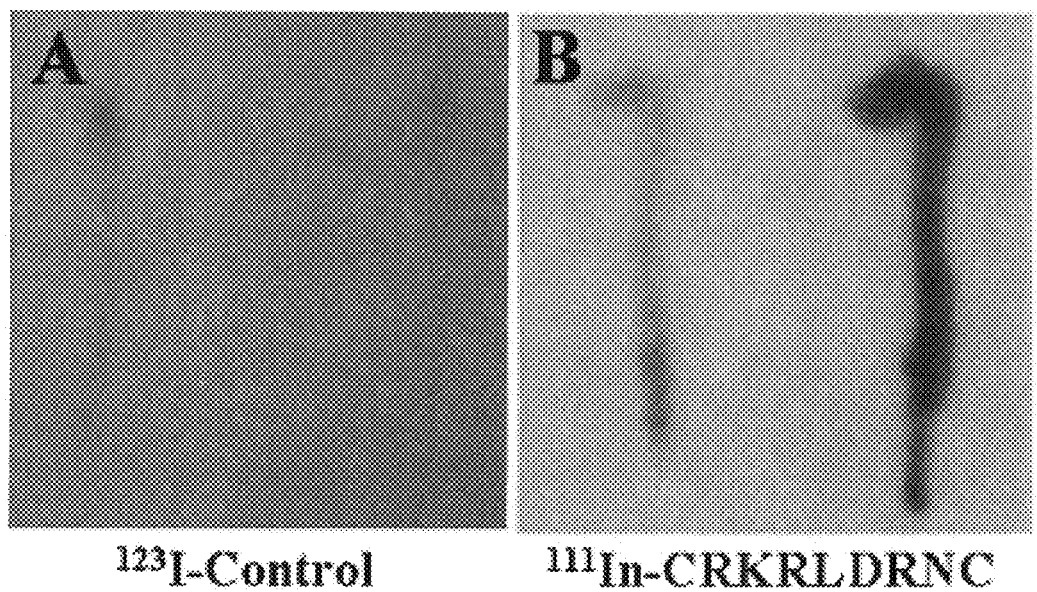

H: Fluorescence micrograph for murine pulmonary tissues with injection of the peptide of the present invention. Blue fluorescence represents nuclear DAPI staining;

FIG. 4 is a micrograph showing confirmation results for in vivo targetability of a radioisotope ($^{123}$I or $^{111}$In)-labeled control peptide and peptide of the present invention to atherosclerotic plaque tissues, in atherosclerosis-induced Ldlr−/− mice.

A: Normal mice (left) and atherosclerotic mice (right) with injection of a radioisotope $^{123}$I-labeled control peptide.

Figure 5:
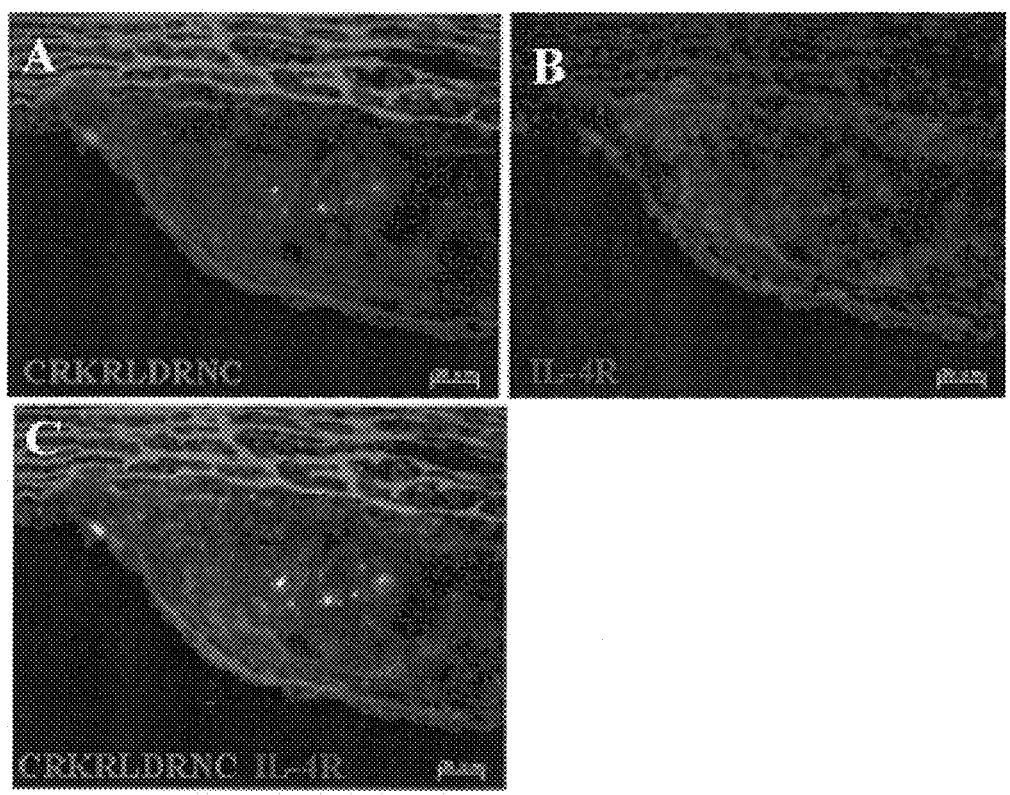

B: Normal mice (left) and atherosclerotic mice (right) with injection of a radioisotope $^{111}$In-labeled peptide of the present invention;

FIG. 5 is a micrograph showing comparison of in vivo targeting sites of a FITC-labeled peptide of the present invention to atherosclerotic plaque tissues and interleukin-4 receptor (IL-4R) sites, in atherosclerosis-induced mice (Ldlr(−/−)).

A: Fluorescence micrograph of tissues after DAPI (blue) staining of atherosclerotic plaque tissues which were targeted by the peptide of the present invention (green).

B: Fluorescence micrograph of tissues after staining of atherosclerotic plaque tissues with antibodies (red) directed against IL-4R and DAPI (blue).

Figure 6:
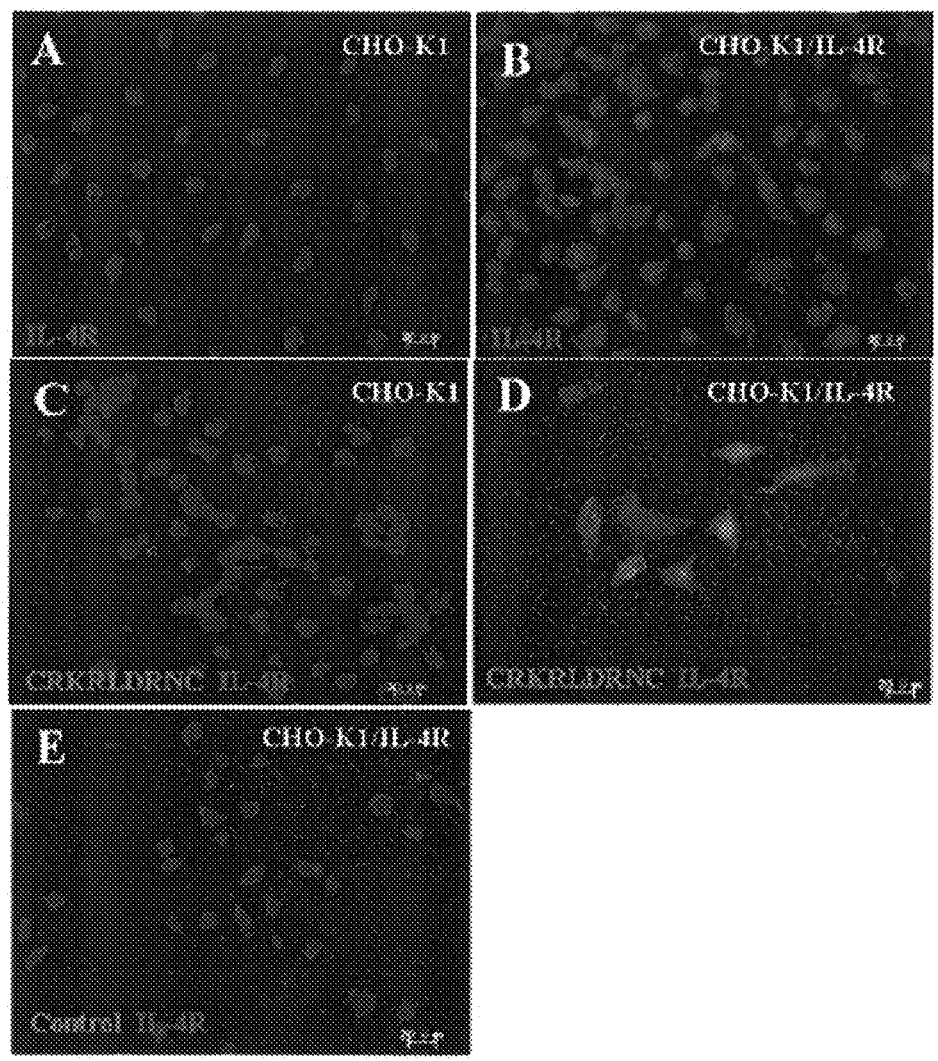

C: Computer-aided combined image of FIGS. 5A and 5B;

FIG. 6 is a micrograph showing selective binding of a peptide of the present invention to CHO-K1 cells which exhibit expression or no expression of IL-4R.

A: Micrograph of CHO-K1 cells exhibiting no expression of IL-4R after staining of cells with antibodies (red) directed against IL-4R.

B: Micrograph showing staining of CHO-K1 cells (CHO-K1/IL-4R) exhibiting artificial expression of IL-4R with antibodies (red) directed against IL-4R.

C: Computer-aided combined image of two microscopic images obtained after reacting of CHO-K1 cells exhibiting no expression of IL-4R with the peptide (green) of the present invention and staining of the cells with antibodies (red) directed against IL-4R.

D: Computer-aided combined image of two microscopic images obtained after reacting of CHO-K1/IL-4R cells exhibiting artificial expression of IL-4R with the peptide (green) of the present invention and staining of the cells with antibodies (red) directed against IL4R.

Figure 7:
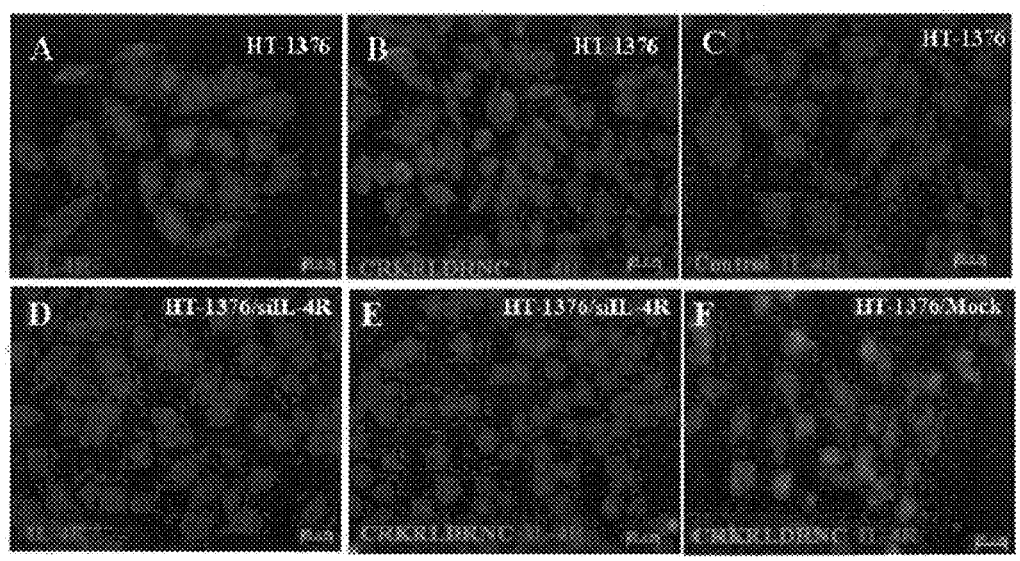

E: Computer-aided combined image of two microscopic images obtained after reacting of CHO-K1/IL-4R cells exhibiting artificial expression of IL-4R with a control peptide (green) and staining of the cells with antibodies (red) directed against IL-4R;

FIG. 7 is a micrograph showing comparison of selective binding of a peptide of the present invention to HT-1376 cells having inhibited expression of IL-4R.

A: Staining of HT-1376 cells, which exhibit endogenous expression of IL-4R, with antibodies (red) directed against IL-4R.

B: Computer-aided combined image of two microscopic images obtained after reacting of HT-1376 cells with the peptide (green) of the present invention and staining of IL-4R with antibodies (red).

C: Computer-aided combined image of two microscopic images obtained after binding of HT-1376 cells with a control peptide (green) and staining of IL-4R with antibodies (red).

D: Antibody (red)-stained IL-4R in HT-1376 cells having inhibited expression of IL-4R via transfection of siRNA against IL-4R.

E: Computer-aided combined image of two microscopic images obtained after reacting of HT-1376 cells having inhibited expression of IL-4R, via transfection of siRNA against IL-4R, with the peptide (green) of the present invention and staining of IL-4R with antibodies (red).

Figure 8:
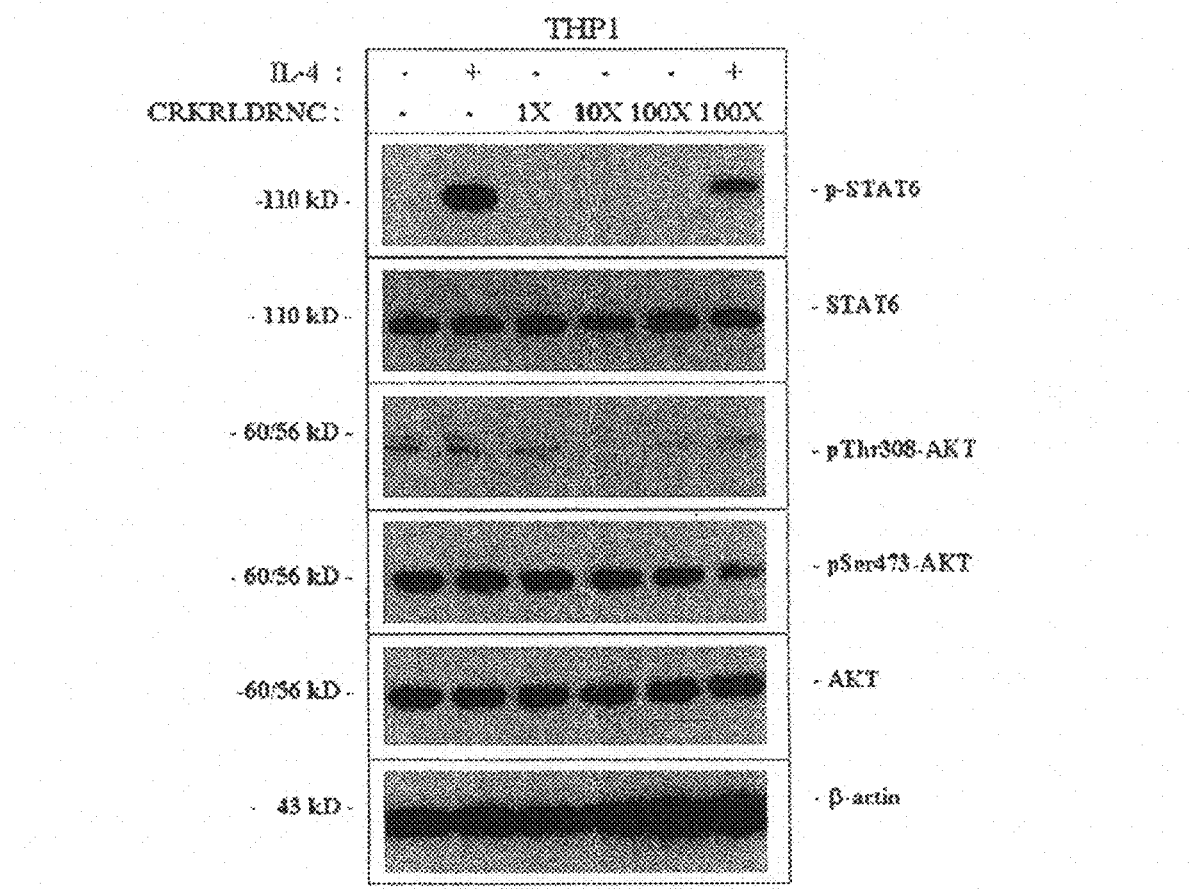
Figure 9:
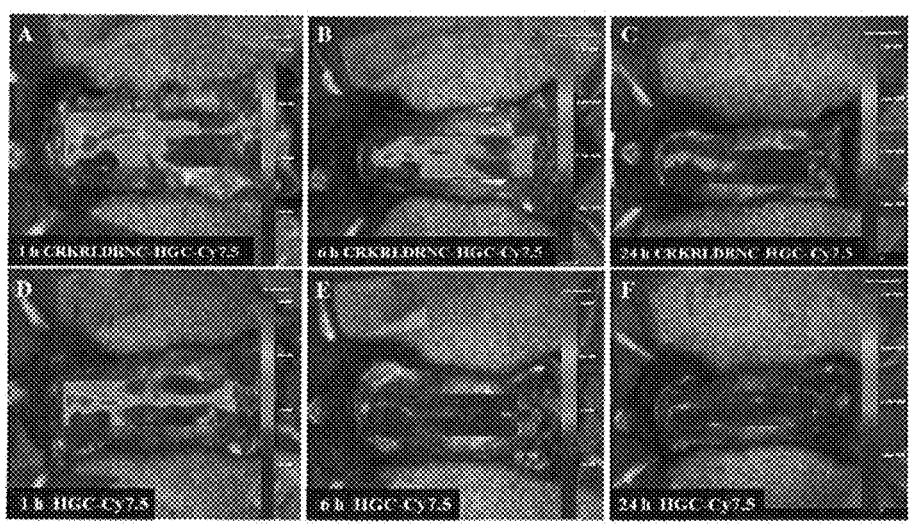

F: Computer-aided combined image of two microscopic images obtained after binding of HT-1376 cells, which exhibit no inhibition of IL-4R via control (mock) siRNA transfection, with the peptide (green) of the present invention and staining of IL-4R with antibodies (red);

FIG. 8 shows the examination results for the antagonistic action of a peptide of the present invention on IL-4-induced phosphorylation of intracellular STAT-6 and AKT signaling proteins, in THP-1 monocytes differentiated into macrophages. (p-STAT6: phosphorylated STAT6; pThr308-AKT: AKT with phosphorylation of an amino acid (Thr) residue at position 308; and pSer473-AKT: AKT with phosphorylation of an amino acid (Ser) residue at position 473);

FIG. 9 is an in vivo image for targeting of nanoparticles labeled with both a peptide of the present invention and a near-infrared fluorescent dye to atherosclerotic plaque tissues, in atherosclerosis-induced Ldlr−/− mice.

A: In vivo image of an aortic region taken 1 hour after injection of Peptide 1 (Inventive)/near-infrared fluorochrome (Cy7.5)-labeled HGC nanoparticles (Peptide 1-HGC-Cy7.5; red) into mouse tail vein.

B: In vivo image of an aortic region taken 6 hours after injection of Peptide 1 (Inventive)/near-infrared fluorochrome (Cy7.5)-labeled HGC nanoparticles (Peptide 1-HGC-Cy7.5; red) into mouse tail vein.

C: In vivo image of an aortic region taken 24 hours after injection of Peptide 1 (Inventive)/near-infrared fluorochrome (Cy7.5)-labeled HGC nanoparticles (Peptide 1-HGC-Cy7.5; red) into mouse tail vein.

D: In vivo image of an aortic region taken 1 hour after injection of near-infrared fluorochrome (Cy7.5)-labeled HGC nanoparticles (HGC-Cy7.5;-red) into mouse tail vein.

E: In vivo image of an aortic region taken 6 hours after injection of near-infrared fluorochrome (Cy7.5)-labeled HGC nanoparticles (HGC-Cy7.5; red) into mouse tail vein.

F: In vivo image of an aortic region taken 24 hours after injection of near-infrared fluorochrome (Cy7.5)-labeled HGC nanoparticles. (HGC-Cy7.5; red) into mouse tail vein.

BEST MODE

Hereinafter, the present invention will be described in more detail.

The present invention provides a novel peptide which is capable of targeting atherosclerotic plaques, and is prophylactically and therapeutically effective for IL-4-mediated inflammatory diseases, particularly atherosclerosis.

The peptide of the present invention may comprise an amino acid sequence having CRKRLDRNC (SEQ ID NO: 1) or CPSNGKRDC (SEQ ID NO: 2) consisting of 9 amino acid residues. The peptide of the present invention specifically binds to atherosclerotic plaque tissues in vitro and in vivo. In one embodiment of the present invention, it was confirmed that a phage (FIG. 2) with insertion of the peptide of the present invention screened by the phage peptide display, or the peptide of the present invention labeled with a fluorescent dye or a radioisotope is capable of targeting atherosclerotic plaques in atherosclerotic mice in vivo (FIGS. 3 and 4). In another embodiment of the present invention, it was confirmed that a binding site of the peptide and the IL-4R site are substantially identical to each other, when the peptide of the present invention is injected into the blood of atherosclerotic mice, and an atherosclerotic plaque tissue is removed and stained with antibodies directed against IL-4R (FIG. 5). Further, when the peptide of the present invention is allowed to react with cells which exhibit artificial expression of IL-4R or removal of IL-4R, the peptide of the present invention specifically binds only to the cells in which IL-4R is present, thus confirming that IL-4R is a receptor for the peptide of the present invention (FIGS. 6 and 7).

The peptide of the present invention may be prepared by a chemical synthesis method known in the art (Creighton, Proteins; Structures and Molecular Principles, W. H. Freeman and Co., NY, 1983). Typical examples of such a peptide synthesis method may include, but are not limited to, liquid or solid-phase synthesis, fragment condensation, and F-MOC or T-BOC chemistry (Chemical Approaches to the Synthesis of Peptides and Proteins, Williams et al., Eds., CRC Press, Boca Raton Fla., 1997; and A Practical Approach, Atherton & Sheppard, Eds., IRL Press, Oxford, England, 1989).

Further, the peptide of the present invention may be prepared by a genetic engineering technique. First, a DNA sequence encoding the aforesaid peptide is constructed according to a conventional method. The DNA sequence may be constructed by PCR amplification using appropriate primers. Alternatively, the DNA sequence may also be synthesized by a standard method known in the art, for example, an automated DNA synthesizer (commercially available from Biosearch or Applied Biosystems). Then, the thus-constructed DNA sequence is inserted into a vector comprising one or more expression control sequences (for example, promoters, enhancers, etc.) being operatively linked to the aforesaid DNA sequence and regulating the expression of the DNA sequence, and a host cell is then transformed with the resulting recombinant expression vector. The resulting transformants are cultured under medium and culture conditions suitable to induce the expression of the DNA sequence, and then a substantially pure peptide encoded by the DNA sequence is recovered from the cell culture. The recovery of peptide can be carried out by a conventional method known in the art (for example, chromatography). As used herein, the term "substantially pure peptide" means that the peptide according to the present invention is substantially free from any other proteins derived from the host. The genetic engineering method for synthesis of the peptide of the present invention can be found in the following literature: Maniatis et al., Molecular Cloning; A Laboratory Manual, Cold Spring Harbor Laboratory, 1982; Sambrook et al., Molecular Cloning: A-Laboratory Manual, Cold Spring Harbor Press, N.Y., Second (1998) and Third (2000) Edition; Gene Expression Technology, Methods in Enzymology, Genetics and Molecular Biology, Methods, in Enzymology, Guthrie & Fink (eds.), Academic Press, San Diego, Calif., 1991; and Hitzeman et al., J. Biol. Chem., 255:12073-12080, 1990.

Further, the present invention provides a polynucleotide encoding an amino acid sequence as set forth in SEQ ID NO: 1 or SEQ ID NO: 2, an expression vector comprising the aforesaid polynucleotide, and a transformant which is transformed with the aforesaid expression vector.

The polynucleotide can be obtained according to the method as described above. Preferably, each of the polynucleotides may have a base sequence as set forth in SEQ ID NO: 3 (5'-TGCCGTAAGCGTCTTGATCGGAATTGC-3') or SEQ ID NO: 4 (5'-TGCCGGACTAGGAGTAAGTCGGGT-TGC-3'). The expression vector refers to plasmid, virus or any vector known in the art, which is capable of expressing the inserted nucleic acid in a host cell. For example, the expression vector may be one in which the polynucleotide encoding the peptide of the present invention is operatively linked to a common expression vector known in the art. The expression vector may generally comprise a replication origin capable of being replicated in the host cell, one or more expression control sequences (for example, promoters, enhancers, etc.) regulating the expression of the DNA sequence, a selective marker, and a polynucleotide encoding the peptide of the present invention being operatively linked to the expression control sequence(s). The transformant may be one which is transformed by the aforesaid expression vector. Preferably, the transformant can be obtained by introducing an expression vector comprising the polynucleotide encoding the peptide of the present invention into a host cell, by using any method known in the art, such as transient transfection, microinjection, transduction, cell fusion, calcium phosphate precipitation, liposome-mediated transfection, DEAE dextran-mediated transfection, polybrene-mediated transfection, electroporation, gene gun, and any known means for intracellular incorporation of nucleic acid (Wu et al., *J. Bio. Chem.*, 267:963-967, 1992; and Wu and Wu, *J. Bio. Chem.*, 263: 14621-14624, 1988).

Further, the present invention provides a composition for diagnosis of atherosclerosis, comprising the peptide of the present invention as an active ingredient. As used herein, the term "diagnosis" refers to the act of identifying the presence or nature of a pathological condition. For the purpose of the present invention, diagnosis is intended for identifying the presence or nature of atherosclerosis. The peptide contained in the diagnostic composition of the present invention may have an amino acid sequence as shown in SEQ ID NO: 1 or SEQ ID NO: 2, and may be one obtained by chemical or genetic engineering methods, as mentioned above. The peptide of the present invention is usefully targeted for atherosclerotic plaques, and therefore may be beneficial for diagnosis of atherosclerosis. The diagnostic composition may further comprise a buffer or reaction liquid to stably maintain a structure and physiological activity of the peptide, in addition to the peptide of the present invention. In order to maintain stability of the peptide, the composition may be present in a powder form or in a dissolved form in any appropriate buffer, or otherwise may be maintained at a constant-temperature of 4° C.

In order to easily confirm, detect and quantify whether the peptide of the present invention binds to atherosclerotic plaque tissues, the peptide of the present invention may be labeled with a label. That is, the peptide may be linked to a detectable label, for example by covalent linking or crosslinking. Examples of the detectable labels may include chromogenic enzymes (such as peroxidase and alkaline phosphatase), radioisotopes (such as $^{124}$I, $^{125}$I, $^{111}$In, $^{99m}$Tc, $^{32}$P, and $^{35}$S), chromophores, biotins, and luminescent or fluorescent dyes (such as FITC, RITC, rhodamine, Texas Red, fluorescein, phycoerythrin, and quantum dots), MR contrast agents (such as superparamagnetic iron oxides (SPIO) and ultrasuperparamagnetic iron oxides (USPIO)). Alternatively, examples of the detectable labels may include antibody epitopes, substrates, cofactors, inhibitors and affinity ligands. Labeling may be carried out during synthesis of the peptide of the present invention, or otherwise may be additionally carried out for an already-synthesized peptide. When it is desired to use a fluorescent dye as the detectable label, diagnosis of atherosclerosis may be made by fluorescence-mediated tomography (FMT). For example, the peptide of the present invention labeled with the fluorescent dye is circulated into the blood of the subject, and then peptide-derived fluorescence may be observed by FMT. If fluorescence is observed, the subject will be diagnosed with atherosclerosis. Further, when it is desired to use a radioactive material as the detectable label, diagnosis of atherosclerosis may be made through observation of peptide-derived radioactivity by positron emission tomography (PET). In this case, it will be possible to achieve more sensitive diagnosis and molecular imaging of atherosclerotic lesions.

Further, the present invention provides a pharmaceutical composition for prevention and treatment of atherosclerosis, comprising the peptide of the present invention and an anti-atherosclerotic drug being conjugated to the peptide, as active ingredients.

The pharmaceutical composition according to the present invention may comprise a therapeutically effective amount of the peptide of the present invention alone or together with the anti-atherosclerotic drug being conjugated to the peptide. As used herein, the term "therapeutically effective amount" refers to an amount which is capable of producing the desired therapeutic response greater than that exhibited by a negative control. Preferably, the therapeutically effective amount is a dose sufficient to prevent or treat atherosclerosis.

Due to targetability to atherosclerotic plaques, the peptide of the present invention can be used as an intelligent drug delivery system which selectively delivers the drug to the atherosclerotic plaque tissues. Accordingly, when the peptide of the present invention is conjugated to a conventional anti-atherosclerotic drug, the drug is selectively delivered only to the atherosclerotic plaque tissues by the peptide of the present invention, so it is possible to enhance the efficacy of the therapeutic drug while achieving a significant reduction of adverse side effects of the drug on normal tissues.

There is no particular limit to the drug that can be conjugated to the peptide of the present invention, as long as it is used in conventional anti-atherosclerotic therapy. Examples of such a drug may include, but are not limited to, anti-proliferative drugs against growth of vascular smooth muscle cells, such as Rapamycin, cholesterol synthesis-inhibiting and blood cholesterol-lowering drugs such as Lovastatin, anti-inflammatory drugs such as Celebrex, and antiplatelet drugs such as Ticlopidine.

Conjugation of the peptide with the anti-atherosclerotic drug may be carried out by a method known in the art, for example, covalent linking or crosslinking. The peptide of the present invention and the anti-atherosclerotic drug may be directly conjugated to each other, or otherwise may be indirectly conjugated via a suitable medium. In addition, the peptide-drug conjugation may be carried out in vitro, or otherwise the peptide of the present invention and the anti-atherosclerotic drug may be separately administered and then conjugated in vivo. For this purpose, the peptide or anti-atherosclerotic drug may be chemically modified without loss of the activity thereof, if necessary.

In order to easily confirm whether the peptide of the present invention binds to the atherosclerotic plaque tissues and therefore the anti-atherosclerotic drug is optimally administered, the peptide of the present invention can be supplied in a labeled state as described above.

Amounts of the peptide and anti-atherosclerotic drug in the composition of the present invention may vary depending upon kinds and amounts of the drug to be conjugated. Preferably, the amount of the drug may be an amount that is sufficiently delivered to the atherosclerotic plaque tissues, and thereby exerts therapeutically effective effects. However, an effective dose of the drug is determined taking into consideration various factors such as administration routes and treatment times, age, weight, health and sex of patients, severity of disease, diet, and excretion rates. Based on these factors, one of ordinary skill in the art can readily determine an optimal effective dose of the peptide of the present invention in compliance with desired therapeutic applications for treatment of atherosclerotic plaques by conjugation of the peptide with the drug.

There is no particular limit to formulations, administration routes and administration methods, as long as the drug delivery composition comprising the peptide of the present invention exhibits desired effects of the present invention. For example, the peptide of the present invention may be orally or parenterally administered. In order to prevent degradation of the peptide which may occur by gastrointestinal digestive enzymes upon oral administration, the peptide of the present invention is preferably composed of L-amino acid residues. Examples of the parenteral administration may include subcutaneous injection, intramuscular injection, and intravenous injection. Preferred is intravenous injection.

When the pharmaceutical composition of the present invention is administered via an oral route, the pharmaceutical composition of the present invention in conjunction with any orally acceptable vehicle may be formulated into various dosage forms such as powders, granules, tablets, pills, dragees, capsules, solutions, gels, syrups, suspensions, and wafers, according to a conventional method known in the art. Examples of suitable vehicles may include various kinds of fillers, for example sugars such as lactose, dextrose, sucrose, sorbitol, mannitol, xylitol, erythritol and maltitol; starches such as corn starch, wheat starch, rice starch and potato starch; cellulose substances such as cellulose, methyl cellulose, sodium carboxymethyl cellulose and hydroxypropyl methyl cellulose; gelatin, polyvinylpyrrolidone (PVP) and the like. If desired, there may be added disintegrating agents such as cross-linked polyvinylpyrrolidone, agar, and alginic acid or sodium alginate. Further, the pharmaceutical composition may further comprise anticoagulants, lubricants, wetting agents, fragrances, emulsifiers and preservatives.

When the pharmaceutical composition of the present invention is administered via a parenteral route, the pharmaceutical composition of the present invention in conjunction with any parenterally acceptable vehicle may be formulated into, for example, an injectable preparation, according to a conventional method known in the art. Upon formulation of the injectable preparation, sterilization must be performed in conjunction with protection of the pharmaceutical preparation from microbial contamination including pathogenic bacteria and fungi. Examples of the vehicle suitable for the injectable preparation may include, but are not limited to, solvents or dispersion media including water, ethanol, polyols (such as glycerol, propylene glycol, and liquid polyethylene glycol), mixtures thereof and/or vegetable oil. More preferably, examples of the suitable vehicle may include isotonic solutions such as Hank's solution, Ringer's solution, PBS (phosphate buffered saline) containing triethanolamine, sterile water for injection, 10% ethanol, 40% propylene glycol and 5% dextrose. In order to protect the injectable preparation against microbial contamination, the preparation may further comprise various antibacterial and antifungal agents, for example, parabens, chlorobutanol, phenol, sorbic acid, thimerosal, and the like. In many cases, it will be preferable to include isotonic agents, for example, sugar or sodium chloride.

Other pharmaceutically acceptable vehicles can be found in the literature (Remington's Pharmaceutical Sciences, 19th ed., Mack Publishing Company, Easton; PA, 1995).

Further, the composition of the present invention may further comprise one or more pharmaceutically acceptable carriers which are typically added to conventional pharmaceutical compositions. As used herein, the term "pharmaceutically acceptable" means that the compound is physiologically acceptable, and does not cause allergic reactions (such as gastrointestinal disorders, and vertigo) or similar reactions, when it is administered to humans or animals. The pharmaceutically acceptable carrier for the injectable preparation may include buffers (e.g. saline or PBS), carbohydrates (e.g. glucose, mannose, sucrose or dextran), antioxidants, bacteriostatic agents, chelating agents (e.g. EDTA or glutathione), adjuvants (e.g. aluminum hydroxide), suspending agents, thickening agents, preservatives, analgesic, solubilizers, isotonic agents and/or stabilizers. In this manner, formulations of the composition comprising the peptide of the present invention can be prepared in various forms. For example, the injection solution can be prepared in the form of a single-dose ampoule or a multi-dose ampoule. The drug delivery composition comprising the peptide of the present invention may be administered by a conventional drug administration method known in the art.

Additionally, the pharmaceutical composition of the present invention may be appropriately formulated by a conventional method known in the art, such that it is possible to achieve fast, sustained or delayed release of active ingredients after administration of the composition to mammal.

Further, the present invention provides a kit for diagnosis of atherosclerosis, comprising the aforesaid peptide of the present invention. The peptide contained in the diagnostic kit of the present invention may have an amino acid sequence as set forth in SEQ ID NO: 1 or SEQ ID NO: 2, and may be one obtained by chemical or genetic engineering methods, as mentioned above. The diagnostic kit may further comprise a buffer or reaction liquid to stably maintain a structure and physiological activity of the peptide. Further, in order to maintain stability of the peptide, it may be supplied in a powder form or in a dissolved form in any appropriate buffer, or otherwise may be maintained at a constant temperature of 4° C.

In order to achieve convenient confirmation, detection and quantification of the peptide of the present invention bound to atherosclerotic plaque tissues, the peptide of the present invention may be labeled with a detectable tag, as mentioned above.

On the other hand, when the peptide of the present invention is used without being labeled, the atherosclerosis diagnostic kit of the present invention may further comprise an ingredient to detect the binding of the peptide to atherosclerotic sites, particularly atherosclerotic plaques, or the location of the peptide, in vivo or in vitro. The additional ingredient may be a known compound for labeling the peptide of the present invention, or antibodies against the peptide of the present invention or IL-4R binding to the peptide of the present invention, as needed for detection through an antigen-antibody reaction, or secondary antibodies against the peptide or IL-4R antibodies, and detection reagents for them. Herein, label materials and related compounds for the peptide of the present invention are as defined above.

Further, secondary antibodies used in the antigen-antibody reaction may be anti-human IgG antibodies which were raised in rats, mice, rabbits, bovine, pigs, goats and the like. Examples of the detection reagent may include coloring or chromogenic agents and buffers. The above-mentioned secondary antibodies may be conjugated with chromogenic enzymes (such as peroxidase, and alkaline phosphatase, AP), radioisotopes (such as $^{125}$I, $^{32}$P, and $^{35}$S), chromophores, biotins, and fluorescent dyes (such as FITC, RITC, rhodamine, Texas Red, fluorescein, and phycoerythrin). Detection of the enzymatic reaction and fluorescent reaction may be carried out using a conventional method known in the art.

If necessary, the kit of the present invention may further comprise a tube for mixing of individual ingredients, a well plate, instructions including how to use the kit, and the like.

Experimental procedures, reagents and reaction conditions that can be used in the above-mentioned methods are conventionally known in the art and will be apparent to those skilled in the art.

Further, the present invention provides a method for detecting atherosclerotic plaques, comprising: injecting the peptide of the present invention into an individual subject; and detecting the location of the peptide in the subject.

There is no particular limit to a method for introduction of the peptide of the present invention into an individual subject. For example, introduction of the peptide may be carried out by administering the peptide of the present invention, which was formulated into an injectable preparation as described above, to the subject via intravenous injection.

There is no particular limit to a method for detecting the location of the peptide in the individual subject. As discussed hereinbefore, localization of the peptide in the subject may be carried out by fluorescence-mediated tomography (FMT) when a fluorescent dye is used as a detectable label, or may be carried out through observation of peptide-derived radioactivity by positron emission tomography (PET), when a radioactive material is used as a detectable label. For this purpose, the peptide of the present invention, as described above, may be tagged with a detectable label.

Meanwhile, the peptide of the present invention has antagonistic effects on IL-4-mediated signaling of cellular inflammatory reaction and survival reaction (see Example 4 and FIG. 8). Therefore, the present invention provides a pharmaceutical composition for prevention and treatment of IL-4-mediated inflammatory diseases, comprising the peptide of the present invention as an active ingredient.

The pharmaceutical composition according to the present invention may comprise a therapeutically effective amount of the peptide of the present invention. As used herein, the term "therapeutically effective amount" refers to an amount which is capable of producing the desired therapeutic response greater than that exhibited by a negative control. Preferably, the therapeutically effective amount is a dose sufficient to prevent or treat an IL-4-mediated inflammatory disease. The IL-4-mediated inflammatory disease may be atherosclerosis. There is no particular limit to a content of an active ingredient in the pharmaceutical composition, formulations, administration routes and administration methods. According to the description as detailed above, these factors may be easily appreciated and determined by those skilled in the art.

Interleukin-4 (IL-4) is a cytokine having various immunomodulatory functions, which is secreted by T-helper2 (Th2) lymphocytes, eosinophils, mast cells, and the like. IL-4 induces differentiation of naive T-helper (nave Th) into Th2 lymphocytes, and production of cytokines such as IL-4, IL-5, IL-9, and IL-13. Further, IL-4 elicits B lymphocyte-mediated secretion of immunoglobulin E (IgE). Particularly in asthma, IL-4 promotes expression of a gene of mucin which is a mucoprotein, and secretion of mucus, thereby playing an important role in airway obstruction and inflammation (Paul, Blood, 1991; 77:1859-1870). That is, IL-4 is a major factor responsible for allergic inflammatory reactions. Therefore, IL-4 may be usefully applied to treatment of allergic diseases if IL-4-mediated effects can be appropriately suppressed.

IL-4 is found at a higher concentration in, atherosclerotic lesion tissues than normal tissues, and induces expression of VCAM-1 and MCP-1 in vascular endothelial cells to thereby facilitate migration of monocytes, T lymphocytes, basophils and eosinophils to inflammatory sites (Sasaguri et al., Atherosclerosis, 1998; 138:247-253; and Lee et al., J Mol Cell Cardiol, 2001; 33:83-94). More importantly, it was reported that when genetic deficiency of IL-4 is introduced into an LDL receptor or ApoE-deficient atherosclerosis mouse model, a size of the aortic atherosclerotic lesion decreases (Davenport et al., Am J Pathol, 2003; 163:1117-1125; and King et al., Arterioscler Thromb Vasc Biol, 2002; 22:456-461). As such, IL-4 is implicated in the atherosclerotic development, and it will be prophylactically and therapeutically effective for atherosclerosis if the action of IL-4 can be antagonized.

There are two types of the IL-4 receptor complexes, the type I receptor consisting of IL-4R alpha chain and IL-2R gamma chain, and the type II receptor consisting of IL-4R alpha chain and IL-13R alpha 1 chain. Binding of IL-4 with the receptor results in phosphorylation and activation of STAT6 via the action of intracellular Janus Kinase, and the thus-activated STAT6 migrates to nuclei in the form of a dimer to thereby regulate expression of various genes related to IL-4, consequently increasing inflammation. Further, it is also reported that the STAT6 protein activates AKT/PKB via the action of Janus Kinase to increase a survival reaction of cells (Nelms et al., Annu Rev Immunol, 1999; 17:701-738).

Taken together, the peptide of the present invention exhibits inhibitory effects on phosphorylation of STAT6 which is an important signaling protein that mediates IL-4-induced inflammatory reaction, and on Thr308 and Ser473 phosphorylation of AKT which is an important signaling protein that mediates IL-4-induced cell survival reaction (see Example 4). Accordingly, the peptide of the present invention can be usefully employed for the prevention and treatment of IL-4-mediated inflammatory diseases, particularly atherosclerosis.

[Mode for Invention]

EXAMPLES

Now, the present invention will be described in more detail with reference to the following Examples. These examples are provided only for illustrating the present invention and should not be construed as limiting the scope and spirit of the present invention.

Example 1

Screening of Peptides Having Binding Specificity to Atherosclerotic Plaques 1-1. Construction of Phage Peptide Library In order to find and screen peptides having specificity to atherosclerotic plaques, the present inventors adopted a phage peptide display technique (Smith, *Science,* 228:1315-1317, 1985). The phage peptide display is a technique to display a peptide consisting of several to several tens of amino acid residues on a surface of bacteriophage. Due to a capability to prepare a phage library having various peptides up to 10⁹, the phage peptide display is a useful technique to find and screen a certain peptide which is capable of targeting a desired tissue or tumor, via simultaneous screening of various kinds of peptides.

In order to screen an atherosclerotic plaque tissue-specific peptide, a phage peptide library was constructed according to the following procedure: First, an oligonucleotide coding for a $CX_7C$ peptide having cysteine residues at both termini and containing 7 amino acid residues between two termini was synthesized randomly. Synthesis of the oligonucleotide was carried out by MACROGEN Inc. (Korea). Thereafter, the synthesized oligonucleotide was cloned into a gene encoding a surface protein of T7 415-1b phage to thereby construct a phage peptide library, using a T7Select® phage cloning kit (Novagen, USA) according to the manufacturer's instructions. The thus-constructed phage peptide library was measured to have a diversity of about $5 \times 10^8$ pfu.

1-2. Phage Library Screening

Figure 1A:
Figure 1B:

Plaque tissues were removed from atherosclerotic patients by atherectomy or endarterectomy, and were cut into slices by a knife. The tissues were ground using a tissue homogenizer to prepare a cell suspension. The phage library constructed in Section 1-1 was mixed with the cell suspension and the resulting mixture was reacted at 4° C. for 2 hours. After the reaction was complete, phages which were non-specifically and weakly bound to cells were removed by washing the cells three times with 1 mL of Dulbecco's modified Eagle's medium (DMEM) containing 1% bovine serum albumin (BSA) at room temperature for 5 min. After washing, the cells were treated with 100 µl of DMEM containing 1% NP40 at 4° C. for 10 min, and 900 µl of BL21 *E. coli* culture as a host was then added to recover cell-bound phages. A portion of the selected phages was subjected to titer determination, according to a conventional method known in the art (Phage display, Clackson T and Lowman H B, p. 171, 2004, Oxford University Press, New York). The remainder of the selected phages was amplified to increase the number of cells, and re-detection of phages that bind well to atherosclerotic plaque-derived cells was then repeated 3 to 4 times according to the procedure as above. As a result, it can be seen that when coronary artery and femoral artery plaques are screened three and four times, respectively, a phage titer sequentially and significantly increases, thus showing successful phase library screening (see FIG. 1).

1-3. Determination of DNA Sequence of Phage Clones and Amino Acid Sequence Analysis In order to examine what peptides were displayed on phages screened in Section 1-2, 30 phage clones were randomly selected, and DNAs inserted into the phages were subjected to PCR amplification, followed by DNA sequencing. Here, a primer (AGCGGACCAGATTATCGCTA) of SEQ ID NO: 5 and a primer (AACCCCTCAAGAC-CCGTTTA) of SEQ ID NO: 6 were used as 5' and 3' primers, respectively. PCR was carried out as follows: pre-denaturation of template DNA at 95° C. for 5 min, followed by 35 cycles of denaturation at 94° C. for 50 seconds, annealing at 50° C. for 1 min and extension at 72° C. for 1 min, and final extension at 72° C. for 6 min.

Thereafter, a base sequence of the PCR product was determined by a DNA sequencing company (Bioneer Co., Ltd., Korea). An amino acid sequence was deduced from the thus-determined base sequence. The deduced amino acid sequence was analyzed using a Clustal W program. As a result, peptides of 2 typical clones were obtained and designated SEQ ID NO: 1 and SEQ ID NO: 2, respectively.

Example 2

In Vivo Targeting of Peptide to Atherosclerotic Plaques 2-1. Construction of Atherosclerosis Mouse Model C57BL/6 mice (Ldlr−/−) into which deficiency of a low-density lipoprotein (LDL) receptor was introduced by a genetic engineering technique were fed daily for 10 weeks with 3 g of high-cholesterol diet, thereby inducing atherosclerosis in animals. The high-cholesterol diet was a special animal feed containing 1.25% cholesterol, 15% fat and 0.5% cholate (Oriental Yeast Co., Japan).

2-2. In Vivo Atherosclerotic Targeting of Selected Phage Clones

Phages ($10^{11}$ pfu) with insertion of the peptide (SEQ ID NO: 1 or SEQ ID NO: 2) selected in Section 1-2 of Example 1 were injected via caudal veins into the blood of atherosclerosis-induced mice and normal mice (wild-type) under anesthesia, followed by circulation for 15 min. Thereafter, aorta were removed from each mouse and aortic tissues were ground to collect cells. The cells were treated with 100 µl of DMEM containing 1% NP-40 at 4° C. for 10 min, and 900 µl of BL21 *E. coli* culture as a host was then added to recover cell-bound phages. The recover phages were subjected to titer determination by a conventional method known in the art.

Figure 2:
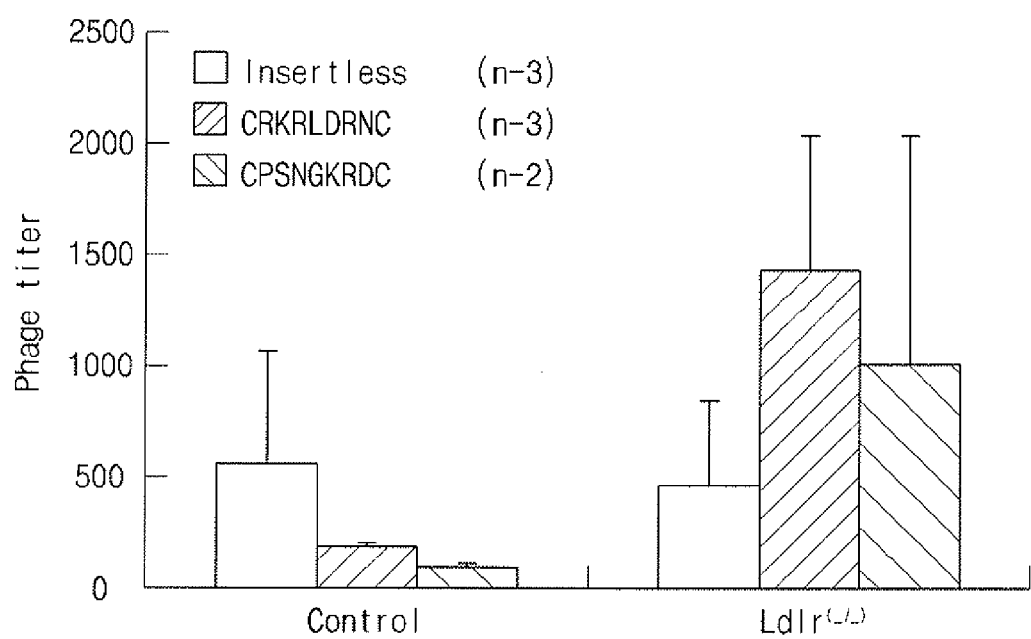
FIG. 2 is a bar graph showing in vivo targetability of phage clones with insertion of a peptide of the present invention to aortic atherosclerotic plaques, in atherosclerosis-induced, low-density lipoprotein (LDL)-receptor-deficient mice (LDL receptor knockout; Ldlr−/−)
Figure 3:
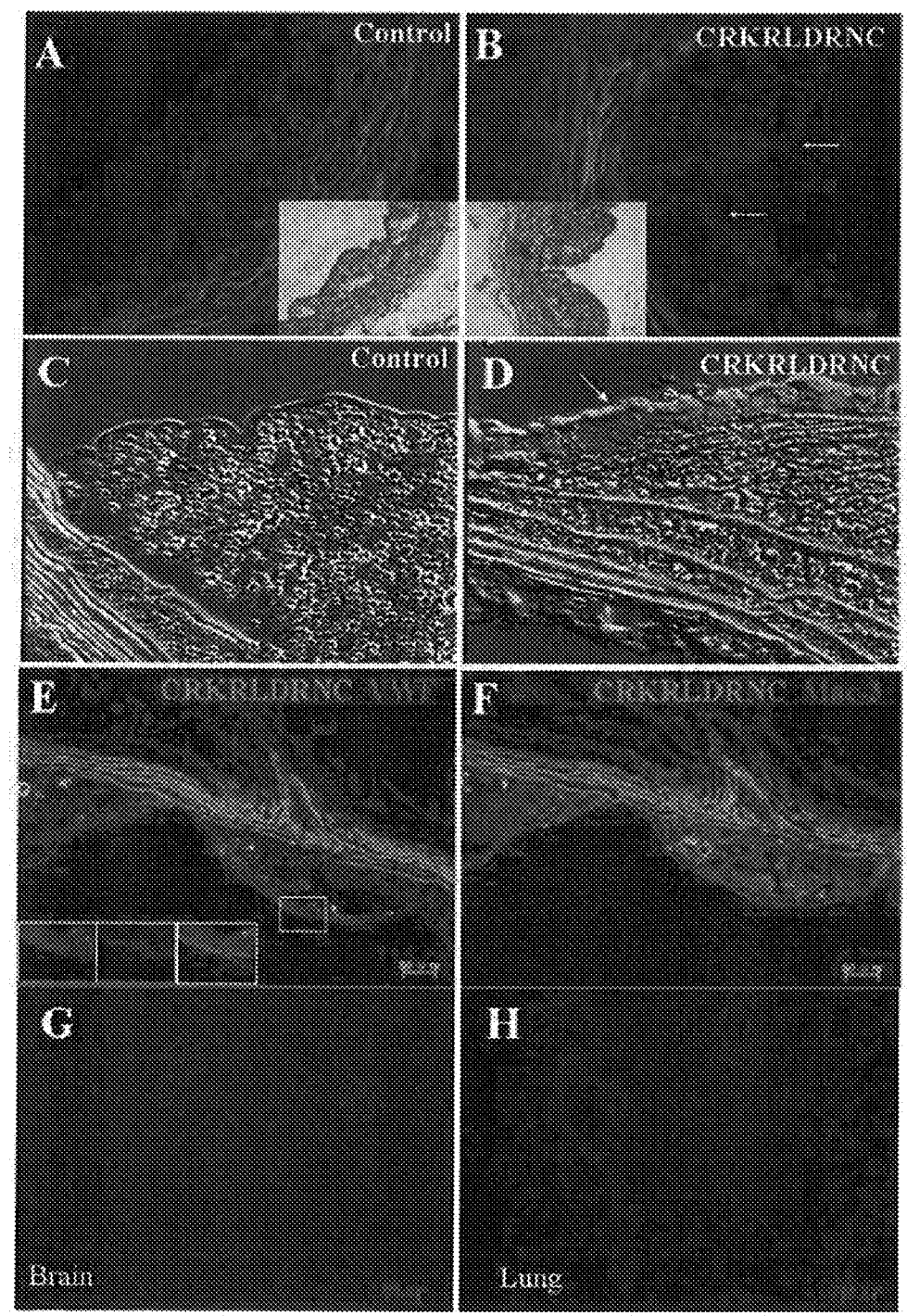
FIG. 3 is a micrograph showing confirmation results of in vivo targetability of a FITC-labeled peptide (SEQ ID NO: 1) of the present invention to atherosclerotic plaque tissues in atherosclerosis-induced mice (Ldlr−/−).

As shown in FIG. 2, the normal mouse group exhibited lower aortic targeting of phages with insertion of the peptide of SEQ ID NO: 1 or SEQ ID NO: 2, as compared to wild-type T7 415-1b phages with no insertion of any gene as a control phage group, whereas the atherosclerosis-induced mice (Ldlr−/−) group exhibited higher aortic targeting of phages with insertion of the peptide of SEQ ID NO: 1 or SEQ ID NO: 2, as compared to a control phage group. Further, it can be seen that phages with insertion of the peptide of SEQ ID NO: 1 or SEQ ID NO: 2 exhibited significantly higher targeting to the aorta of atherosclerotic mice (Ldlr−/−), as compared to the aorta of the normal mouse group; Here, a titer for the peptide (SEQ ID NO: 1)-inserted phage and the control phage is the overall average value of the results obtained for 3 mice, respectively, whereas a titer for the peptide (SEQ ID NO: 2)-inserted phage is the overall average value of the results obtained for 2 mice.

2-3. In Vivo Atherosclerotic Targeting of Fluorescent Dye-Conjugated Peptide

Out of two phage clones selected in Example 1 and Section 2-1, the peptide of SEQ ID NO: 1 exhibiting more intense atherosclerotic targeting was synthesized at a purity of more than 85% by a peptide synthesis company (Anigen, Korea).

Here, the peptide was synthesized by tagging an N-terminus of the peptide with FITC (fluorescein isothiocyanate) as a green fluorescent dye. The synthesized FITC-CRKRLDRNC peptide and a control peptide (FITC-NSSVDK) at final blood concentrations of 50 µM were injected into the atherosclerosis-induced mice via the left ventricle of animals, followed by circulation for 15 min. Thereafter, the aortae were removed from each mouse, and frozen sections were prepared, followed by Oil Red O (fat marker, Sigma-Aldrich, USA) staining or vWF (vascular endothelial cell marker, 1:5000 dilution, Abcam, USA) and Mac-3 (macrophage marker, 1:50 dilution, BD, USA) staining (Matter et al., Circulation Research, 95:1225-1233, 2004). In order to stain nuclei in tissues, a mounting medium containing a nuclear staining dye, 4',6-diamidino-2-phenylindole (DAPI) (manufactured by Molecular Probe, USA) was treated on a slide, according to a conventional method known in the art, followed by fluorescence microscopic examination.

The results thus obtained are given in FIG. 3.

A: Fluorescence micrograph for murine aortic atherosclerotic plaque tissues with injection of a control peptide. Blue fluorescence represents nuclear DAPI staining, and an inserted small figure represents the results of Oil Red O staining of the same tissues.

B: Fluorescence micrograph for murine aortic atherosclerotic plaque tissues with injection of the peptide of the present invention. Green fluorescence (arrow) represents the peptide, blue fluorescence represents nuclear DAPI staining, and an inserted small figure represents results of Oil Red O staining of the same tissues.

C: DIC (Differential interference contrast) fluorescence micrograph for murine aortic atherosclerotic plaque tissues with injection of a control peptide.

D: DIC fluorescence micrograph for murine aortic atherosclerotic plaque tissues with injection of the peptide of the present invention. Green fluorescence (arrow) represents the peptide.

E: Fluorescence micrograph for murine aortic atherosclerotic plaque tissues with injection of the peptide of the present invention, after double staining of the tissues with antibodies against vascular endothelial cells. Green fluorescence represents the peptide, red fluorescence represents staining of vWF for vascular endothelial cells, and blue fluorescence represents nuclear DAPI staining. Inserted small figures represent enlarged micrographs.

F: Fluorescence micrograph for murine aortic atherosclerotic plaque tissues with injection of the peptide of the present invention, after double staining of the tissues with antibodies against macrophages. Green fluorescence represents the peptide, red fluorescence represents staining of Mac-3 for macrophages, and blue fluorescence represents nuclear DAPI staining.

G: Fluorescence micrograph for mouse cerebral tissues with injection of the peptide of the present invention. Blue fluorescence represents nuclear DAPI staining.

H: Fluorescence micrograph for murine pulmonary tissues with injection of the peptide of the present invention. Blue fluorescence represents nuclear DAPI staining.

As shown in FIG. 3, substantially no control peptide was found in plaque tissues, whereas the peptide of the present invention was more targeted in plaque tissues. However, the peptide of the present invention was not detected in cerebral tissues and pulmonary tissues. Distribution of the peptide observed in the atherosclerotic plaques was similar to that of vascular endothelial cells and macrophages.

2-4. In Vivo Atherosclerotic Targeting of Radioisotope-Conjugated Peptide

In order to evaluate in vivo targetability of an inventive peptide through a higher sensitivity method, the peptide was synthesized and then an N-terminus of the peptide was tagged with a radioisotope ($^{111}$In). The $^{111}$In-tagged peptide of the present invention at a dose of 160 μCi was injected via the tail vein into the blood of atherosclerotic mice and normal mice, followed by circulation for 15 min. Thereafter, aortae were removed from each mouse and autoradiography with X-ray film exposure was carried out. As a control group, the $^{123}$I-tagged peptide ($^{123}$I-CLEVSRKNC) was injected at a dose of 104 μCi.

As shown in FIG. 4, the control peptide exhibited substantially no detection of radioactivity resulting from aortic targeting of the peptide, in the aortae of normal mice and atherosclerotic mice. On the other hand, the peptide of the present invention exhibited detection of remarkably intense radioactivity in the aortae of the atherosclerotic mouse group, as compared to the normal mouse group, thus representing that the peptide of the present invention has atherosclerosis-specific targetability.

Example 3

Evaluation of IL-4R as Peptide Receptor 3-1. Histological Distribution of Peptide and IL-4R In order to ascertain a receptor that binds to the peptide of the present invention, binding of the peptide was examined for various receptors. Out of those receptors, the results for IL-4R are as follows. First, fluorescein (FITC)-conjugated peptide of the present invention at a final concentration of 50 μM was injected into the blood of experimental animals, followed by circulation for 15 min. Thereafter, the aortae were removed from animals, and a frozen section slide was prepared. Then, the tissue section was stained by reaction of the section with antibodies (1:200 dilution, BD, USA) directed against IL-4R, at room temperature for 1 hour. In order to stain the tissue nuclei, DAPI was treated on the slide which was then examined under a fluorescence microscope (Joshi et al., Cancer Research, 61:8058-8061, 2001).

As shown in FIG. 5, the FITC-CRKRLDRNC peptide (green fluorescence) and IL-4R (red fluorescence) were almost identically positioned in atherosclerotic plaque tissues. Blue fluorescence represents nuclear staining. This result suggests that the receptor to which the peptide of the present invention binds is IL-4R.

3-2. Bindability of Peptide to IL-4R-Expressing Cells

In order to further confirm roles of IL-4R as the receptor for the peptide of the present invention, a plasmid capable of expressing IL-4R (Cat. #TC119877, Origene, USA) was introduced into IL-4R-deficient CHO-K1 cells according to a conventional method known in the art, followed by expression of IL-4R, and binding of IL-4R with the peptide of the present invention was examined.

As shown in FIG. 6, IL-4R-expressing CHO-K1 (hereinafter, referred to as "CHO-K1/IL-4R") cells were fixed in a methanol/acetone mixture (1:1 v/v). The cells were stained with antibodies (1:200 dilution) directed against. IL-4R and cell nuclei were stained with DAPI, followed by fluorescence microscopic examination. As a result, a large amount of IL-4R (red fluorescence) was present on the cell surface (FIG. 6B). Next, CHO-K1 and CHO-K1/IL-4R cells were reacted with 10 μM of the FITC-C-RKRLDRNC peptide at room temperature for 1 hour. Upon fluorescence microscopic examination, CHO-K1/IL-4R cells exhibited green fluorescence due to the peptide and red fluorescence due to IL-4R (FIG. 6D). On the other hand, IL-4R-deficient CHO-K1 cells exhibited no fluorescence arising from the peptide and IL-4R (FIG. 6C). Further, the control peptide (FITC-NSSVDK) showed no binding with CHO-K1/IL-4R cells (FIG. 6E), even though they were reacted under the same conditions as in the reaction of the peptide of the present invention.

3-3. Bindability of Peptide to Cells that Inhibit Expression of IL-4R

Silencing RNA for IL-4R (Cat. #16708A, Ambion, USA) was introduced into HT-1376 cells that essentially show constitutive expression of IL-4R, according to a conventional method known in the art, and treated for 24 hours to thereby result in substantially no expression of IL-4R, followed by evaluation of peptide binding. More specifically, 10 nM of IL-4R silencing RNA synthesized by the manufacturer was mixed with a siPORT™ NeoFX™ lipid transfection agent (Ambion, USA), and the mixture was treated for 24 hours on HT-1376 cells grown in a 4-well chamber slide, such that IL-4R silencing RNA is incorporated into the cells. Thereafter, the culture medium was replaced with one containing 10% bovine serum and the cells were recovered for 24 hours. After staining of cells with IL-4R antibodies and nuclear DAPI staining under the same conditions as in FIG. 6, a cellular expression level of IL-4R was examined. After IL-4R staining, the FITC-CRKRLDRNC peptide was reacted with the cells under the same conditions as in FIG. 6, and a binding degree of the peptide was measured.

As shown in FIG. 7, the silencing RNA for IL-4R was intracellularly introduced, and the IL-4R silencing RNA-treated HT-1376 (hereinafter, referred to as "HT-1376/siIL-4R") cells were stained with IL-4R antibodies and cell nuclei were stained with DAPI. As a result, it was observed under a fluorescence microscope that the expression level of IL-4R in HT-1376/siIL-4R cells is significantly decreased. When the FITC-CRKRLDRNC peptide was reacted with HT-1376 cells under the same conditions as in FIG. 6, the peptide of the present invention exhibited active binding to the cells (FIG. 7A), but showed substantially no binding to HT-1376/siIL-4R cells (FIG. 7D). On the other hand, the control peptide (FITC-NSSVDK) showed almost no binding to HT-1376 cells (FIG. 7C). Further, the peptide of the present invention still showed good bindability to mock silencing RNA-treated HT-1376 cells (FIG. 7F).

Example 4

IL-4-Induced Phosphorylation of Intracellular Signaling Proteins and Antagonistic Effects of Peptide on IL-4

THP1 monocytes were treated and activated with 100 ng/mL of phorbol myristate acetate (PMA) for 3 days to thereby induce differentiation into macrophages. The culture medium was replaced with a serum-free fresh medium, and the cells were cultured for 18 hours and treated with 0.67 nM of IL-4 alone for 10 min. Meanwhile, the peptide of the present invention alone or in conjunction with IL-4 was treated at concentrations of 0.67 nM (1×, one-fold concentration that of IL-4), 6.7 nM (10×, 10-fold concentration that of IL-4) and 67 nM (100×, 100-fold concentration that of IL-4) on cells which are under the same culture phase. After the reaction was complete, cells were disrupted according to a conventional method known in the art and cell lysates were subjected to electrophoresis and Western blot analysis using antibodies. As assay antibodies, STAT6 antibody and phospho-STAT6 (P-STAT6) antibody (Cell Signaling, USA), AKT antibody and phosphor-Thr308-AKT antibody or phosphor-Ser473 AKT antibody (Santa Cruz, USA) and β-actin antibody were used.

As shown in FIG. 8, there was a significant increase in phosphorylation of STAT6 which is an important signaling protein that mediates IL-4-induced inflammatory reaction, and the peptide of the present invention (at a 100-fold concentration) exhibited significant inhibitory effects on phosphorylation of STAT6. On the other hand, an amount of total STAT6 proteins was not affected. Further, Thr308 and Ser473 phosphorylation of AKT which is an important signaling protein that mediates IL-4-induced cell survival reaction was slightly increased by IL-4, and phosphorylation of AKT was inhibited by the peptide of the present invention at a 100-fold concentration. Particularly, the peptide of the present invention exhibited greater antagonistic effects on Ser473 phosphorylation and Ser473 phosphorylation was inhibited to a lower level than that of the control group which was not treated with IL-4.

Example 5

In vivo Imaging of Atherosclerotic Plaque Targeting Using Peptide/Near-infrared Fluorescent Dye-labeled Nanoparticles First, 5βcholanic acid was added to biodegradable and hydrophilic glycol chitosan (MW: 50 kDa) to thereby prepare hydrophobically-modified glycol chitosan (HGC). Then, N-terminal cysteine of the peptide and HGC nanoparticles were linked together using N-succininidyl 4-(maleimidomethyl)cyclohexanecarboxylate (SMCC; Sigma) as a linker. Further, the near-infrared fluorescent dye Cy7.5 was linked to an amino (—NH) group of the nanoparticles to prepare CRKRLDRNC peptide-HGC-Cy7.5 nanoparticles which will be finally used in experiments of the present invention. 50 mg/kg (BW) of the resulting nanoparticles were injected into tail vein of atherosclerotic mice and circulated. Animals were anesthetized and the thorax and abdomen were excised to make the aortae visible. Then; an in vivo imaging was taken using eXplore Optix™ (GE). As a control group, HGC-Cy7.5 nanoparticles which were labeled with the fluorescent dye Cy7.5 alone, not with the peptide of the present invention, were used.

As shown in FIG. 9, according to the images obtained 1 hour after injection of the nanoparticles into tail vein, both CRKRLDRNC peptide-HGC-Cy7.5 nanoparticles and HGC-Cy7.5 nanoparticles exhibited intense near-infrared fluorescence signals at the aortic sites (FIG. 9, left panels). Upon reviewing the images obtained 6 hours after injection of the nanoparticles, the aortae of mice to which CRKRLDRNC peptide-HGC-Cy7.5 nanoparticles labeled with the peptide of the present invention were administered still showed intense near-infrared fluorescence signals, but the control nanoparticles showed very weak fluorescence signals (FIG. 9, middle panels). 24 hours after injection of the nanoparticles, both groups showed almost no fluorescence signal (FIG. 9, right panels).

As apparent from the above description, the peptide of the present invention effectively targets atherosclerotic plaques, and binds to IL-4R to thereby exhibit antagonistic effects on IL-4-mediated signaling of cellular inflammatory reaction and survival reaction. Therefore, the peptide of the present invention can be used for diagnosis of atherosclerosis, prevention and treatment of IL-4-induced inflammatory reaction and prevention and treatment of atherosclerosis which is primarily caused by the inflammatory reaction, as well as for prevention or treatment of atherosclerosis via conjugation with an anti-atherosclerotic drug.

What is claimed is:

1. A peptide having an amino acid sequence as set forth in SEQ ID NO: 1 or SEQ ID NO: 2.

2. A polynucleotide encoding the amino acid sequence of claim 1.

3. The polynucleotide according to claim 2, wherein the polynucleotide has a base sequence as set forth in SEQ ID NO: 3 or SEQ ID NO: 4.

4. An expression vector comprising the polynucleotide of claim 2.

5. A transformant which is transformed with the expression vector of claim 4.

6. A composition for diagnosis of atherosclerosis, comprising the peptide of claim 1 as an active ingredient.

7. The composition according to claim 6, wherein the peptide is labeled with a label.

8. The composition according to claim 7, wherein the label is selected from the group consisting of peroxidase, alkaline phosphatase, $^{124}$I, $^{125}$I, $^{111}$In, $^{99m}$Tc, $^{32}$P, $^{35}$S, chromophore, biotin, fluorescein isothiocyanate (FITC), rhodamine isothiocyanate (RITC), rhodamine, Texas Red, fluorescein, phycoerythrin, quantum dots, superparamagnetic iron oxides (SPIO) and ultrasuperparamagnetic iron oxides (USPIO).

9. A method of treating atherosclerosis comprising:
administering a pharmaceutical composition to a mammal in need thereof, wherein the pharmaceutical composition contains the peptide of claim 1 and an anti-atherosclerotic drug being conjugated to the peptide, as active ingredients.

10. The method according to claim 9, wherein the anti-atherosclerotic drug is selected from the group consisting of Rapamycin, Lovastatin, Celebrex, and Ticlopidine.

11. A kit for diagnosis of atherosclerosis, comprising the peptide of claim 1 as an active ingredient.

12. The kit according to claim 11, wherein the peptide is labeled with a label.

13. The kit according to claim 12, wherein the label is selected from the group consisting of peroxidase, alkaline phosphatase, $^{124}$I, $^{125}$I, $^{111}$n, $^{99m}$Tc, $^{32}$P, $^{35}$S, chromophore, biotin, fluorescein isothiocyanate (FITC), rhodamine isothiocyanate (RITC), rhodamine, Texas Red, fluorescein, phycoerythrin, quantum dots, superparamagnetic iron oxides (SPIO) and ultrasuperparamagnetic iron oxides (USPIO).

14. A method for detecting atherosclerotic plaques, comprising:
injecting the peptide of claim 1 into an individual subject; and
detecting the location of the peptide of claim 1 in the subject.

15. The method according to claim 14, wherein the peptide is labeled with a label.

16. The method according to claim 15, wherein the label is selected from the group consisting of peroxidase, alkaline phosphatase, $^{124}$I, $^{125}$I, $^{111}$In, $^{99m}$Tc, $^{32}$P, $^{35}$S, chromophore, biotin, fluorescein isothiocyanate (FITC), rhodamine isothiocyanate (RITC), rhodamine, Texas Red, fluorescein, phycoerythrin, quantum dots, superparamagnetic iron oxides (SPIO) and ultrasuperparamagnetic iron oxides (USPIO).

17. A method of treating atherosclerosis comprising:
administering a pharmaceutical composition to a mammal in need thereof, wherein the pharmaceutical composition contains the peptide of claim 1 as an active ingredient.

* * * * *